(12) United States Patent
Mangiardi et al.

(10) Patent No.: US 8,012,106 B2
(45) Date of Patent: Sep. 6, 2011

(54) LUMEN MEASURING DEVICES AND METHODS

(75) Inventors: Eric K. Mangiardi, Charlotte, NC (US); Jason M. Reynolds, Charlotte, NC (US); Ulf R. Borg, Cornelius, NC (US); Tony D. Alexander, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 865 days.

(21) Appl. No.: 11/252,363

(22) Filed: Oct. 17, 2005

(65) Prior Publication Data

US 2007/0106181 A1    May 10, 2007

(51) Int. Cl.
*A61B 5/103* (2006.01)
*A61B 5/117* (2006.01)
*A61B 5/08* (2006.01)
*A61M 25/00* (2006.01)

(52) U.S. Cl. .......... 600/587; 600/484; 600/585
(58) Field of Classification Search .......... 600/117, 600/481, 587, 595
See application file for complete search history.

(56) References Cited

U.S. PATENT DOCUMENTS

| | | | | |
|---|---|---|---|---|
| 4,362,167 A * | 12/1982 | Nicolai et al. | | 600/591 |
| 5,010,892 A * | 4/1991 | Colvin et al. | | 600/587 |
| 5,356,382 A * | 10/1994 | Picha et al. | | 604/105 |
| 5,919,147 A * | 7/1999 | Jain | | 600/587 |
| 6,033,359 A * | 3/2000 | Doi | | 600/117 |
| 6,395,007 B1 * | 5/2002 | Bhatnagar et al. | | 606/94 |
| 6,450,976 B2 * | 9/2002 | Korotko et al. | | 600/587 |
| 7,234,468 B2 * | 6/2007 | Johnson et al. | | 128/877 |
| 2006/0064039 A1 * | 3/2006 | Griego et al. | | 600/587 |

OTHER PUBLICATIONS

EP Communication and Supplementary Partial European Search Report for EP Application No. 04 77 8005, mailed Apr. 14, 2009.
PCT Notification of Transmittal of the International Search Report, PCT International Search Report mailed Jun. 3, 2005 for PCT/USO4/22256 (Filed Jul. 9, 2004).

* cited by examiner

*Primary Examiner* — Max Hindenburg
*Assistant Examiner* — Adam Eiseman
(74) *Attorney, Agent, or Firm* — Stoel Rives LLP (57) ABSTRACT

A lumen measuring device generally includes a central member dimensioned to extend into a lumen and an elongate outer member having a flexible region configured to flex outward from the central member in response to retraction of the central member. In measuring a lumen, the flexible region is caused to contact the lumen. The lumen may be contacted by linear segments that hinge or by members that bow arcuately. A polygon, such as a triangle, may be defined by portions of the outer member and the central member. A handle assembly may be provided by which the disposition of the central member relative to the outer member may be adjusted. Indicators may be defined by the central member and outer member by which the disposition of the central member and by which the diameter of a lumen may be determined.

37 Claims, 4 Drawing Sheets
(3 of 4 Drawing Sheet(s) Filed in Color)

LUMEN MEASURING DEVICES AND METHODS

FIELD OF THE INVENTION

The present invention generally relates to devices and methods for measuring dimensions of a body lumen, and more particularly, to devices and methods of measuring the internal diameter of a lumen at a determinable position along the lumen.

BACKGROUND OF THE INVENTION

Bronchial stents are being used to address various ailments that potentially otherwise may restrict the breathing airways. For example, stents are disposed in the airways of patients suffering from chronic obstructive pulmonary diseases (COPD) and in the esophagi of patients suffering from cancer. Furthermore, the use of stents is on the rise in an expanding range of medical applications. For example, stents are used to keep blood vessels open, they are inserted into ureters to maintain drainage from kidneys, and they are inserted into bile ducts in addressing pancreatic cancer and cholangiocarcinoma (bile-duct cancer). Stents provide comfort and enhance longevity in many medical conditions where no direct cure is available.

Though stents are excellent devices when properly deployed, improper installation with regard to the disposition of a stent relative to its host lumen, or improper sizing of a stent with regard to its dimensions relative to the lumen, can lead to tissue inflammation, tissue granulation, stent migration, and other problems. Once a stent is improperly installed, adjusting its disposition or removing it out of concern for an error in sizing may require an invasive procedure. Proper sizing and placement of a stent are therefore of importance upon first installation.

Beyond initial time periods after a stent placement procedure, the principal importance of stent length as a risk factor for restenosis is becoming apparent, particularly, for example, to interventional radiologists. Typical methods of sizing stents rely on visual estimations from angiograms. Practitioners in this area need devices and methods for determining appropriate stent lengths.

Though excessive length of an endoluminal revascularization device can lead to migration and restenosis, there are also important risk factors associated with vessel diameter. Many practitioners pay more care in determining appropriate stent length than stent diameter. Some physicians generally employ expandable stents that, if allowed to fully expand, are larger than the diameter of the host lumen. This practice can lead to tissue granulation and further vessel damage.

Unfortunately, methods of obtaining luminal dimensions have diverged based on inquiry. Physicians involved in interventional cardiology and interventional radiology in particular have been attempting to find ways to deal with occluded or stenotic coronary arteries, blood vessels, tubular conduits, and other body lumens. The vessel diameter and a frequency shift are often measured with electronic calipers utilizing imaging and Doppler modes, respectively, for the determination of the mean flow rate through a vessel. Practitioners interested in hemodynamics and vessel patency, which relate to fluid flow through a treated segment and may be affected by recurrent stenosis, use alternative tools to measure the diameters of lumens. Often, imaging tests such as CT Scans are used to assist with dimensional calculations. Few devices have been developed that allow for accurate in situ measurement of tissue for the purposes of evaluating vessel patencies and for determining optimal dimensions and positions for interventional prostheses such as stents.

Therefore, there is an existing need for devices and methods for accurately measuring stenosis topography and luminal dimensions so that appropriately dimensioned interventional prostheses may be appropriately placed and installed. There is a need for lumen measuring devices and methods for measuring internal dimensions of a lumen at determinable positions along the length of the lumen.

SUMMARY OF EXEMPLARY EMBODIMENTS

The above needs and other advantages may be achieved by providing lumen measuring devices and methods according to the present invention. A lumen measuring device generally includes a central member dimensioned to extend into a lumen and an elongate outer member extending around the central member. The elongate outer member has a portion fixed to the central member, a portion movably extending around the central member, and a flexible region configured to flex outward from the central member in response to retraction of the central member. In measuring a lumen, the flexible region is caused to contact the lumen. According to one embodiment, the flexible region includes flexing members that arcuately bow outwardly from the central member. According to another embodiment, the flexible region includes generally linear segments that hinge outwardly from the central member. A polygon, such as a triangle, may be defined by portions of the flexible region and the central member, wherein a dimension of a polygon is adjusted by movement of the central member relative to the outer member. A handle assembly may be provided by which the disposition of the central member relative to the outer member can be adjusted.

A lumen measuring device may also include indicators for determining the disposition of the device along a lumen and for determining the disposition of the central member relative to the outer member. In one example, the outer member defines an aperture through which an indicator defined by the central member may be viewed for determining the disposition of the central member relative to the outer member. In another example, an indicator defined by the central member is viewable through the outer member and the disposition of the central member is determined by viewing the central member indicator in relation to indicators defined by the outer member. Indicators may be defined along the outer member for determining the disposition of the device along a host lumen.

A method of measuring an interior dimension of a lumen generally includes the steps of disposing an elongate assembly into a lumen, moving an elongate central member of the assembly relative to an elongate outer member of the assembly causing a region of the outer member to flex such that the lumen is contacted, and measuring an interior dimension of the lumen by determining the disposition of the central member relative to the outer member. The central member preferably includes colored portions and determining the disposition of the central member relative to the outer member preferably includes viewing the colored portions.

The embodiments of the present invention provide many advantages. For example, at least one embodiment of inventive lumen measuring device includes flexing members attached at opposite ends to the device such that medial portions of the flexing members flex outwardly for contacting and measuring a lumen. This is advantageous over lumen measuring devices that have free-ended measuring members constructed of shape-memory materials in that the flexing members of the invention define stable repeatable structures that are predictably or empirically calibrated with regard to measuring the diameter of a lumen. Polygonal structures defined by embodiments of the invention may be particularly advantageous with regard to predictable calibrations, repeatable performances, and accurate measurements of lumen dimensions. For another example of an advantage provided by the invention, indicators for measuring lumens are preferably brightly colorized bands for unambiguous measurements.

BRIEF DESCRIPTION OF THE SEVERAL VIEWS OF THE DRAWINGS

The patent or patent application file contains at least one drawing executed in color. Copies of this patent or patent application publication with color drawing(s) will be provided by the Office upon request and payment of the necessary fee. Having thus described the invention in general terms, reference will now be made to the accompanying drawings, which are not necessarily drawn to scale, and wherein.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
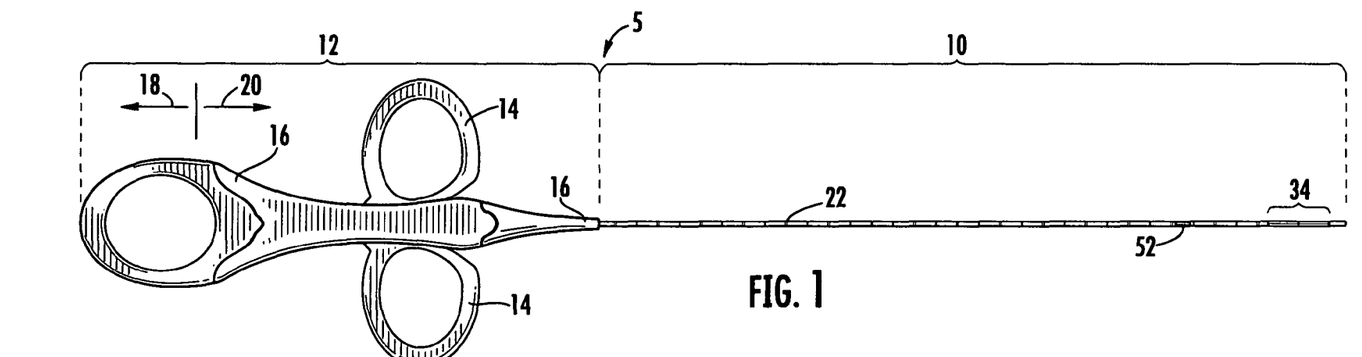
FIG. 1 is a plan view of a lumen measuring apparatus according to an embodiment of the invention, the apparatus having obtained a closed configuration for passage through a working channel of an endoscope and/or bronchoscope and disposition into a lumen.
Figure 2:
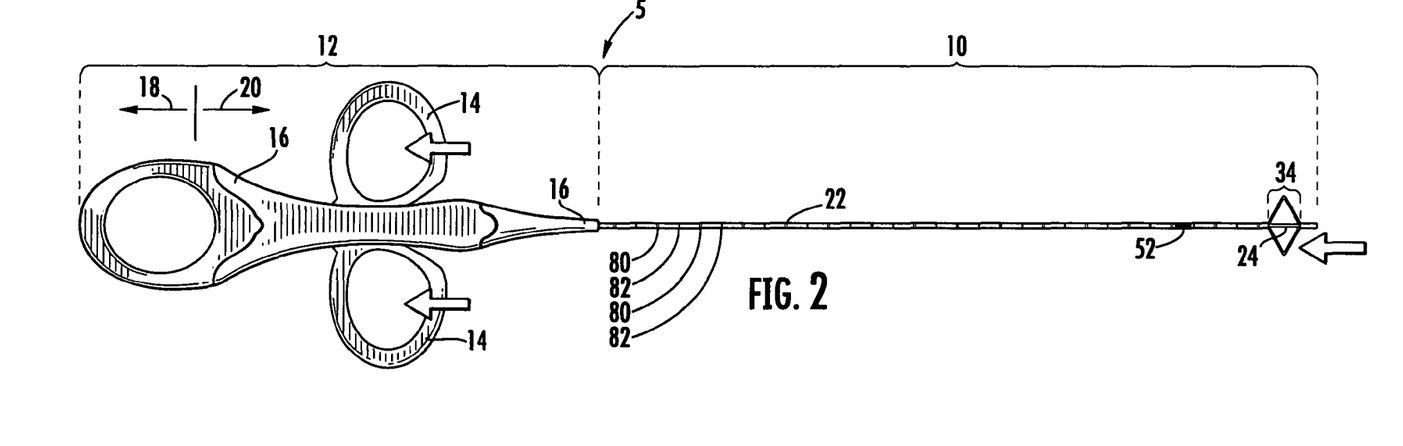
FIG. 2 is a plan view of the apparatus of FIG. 1, having obtained a medially open configuration for measuring the diameter of a lumen by contacting hinged linear segments of the apparatus with the lumen.
Figure 3:
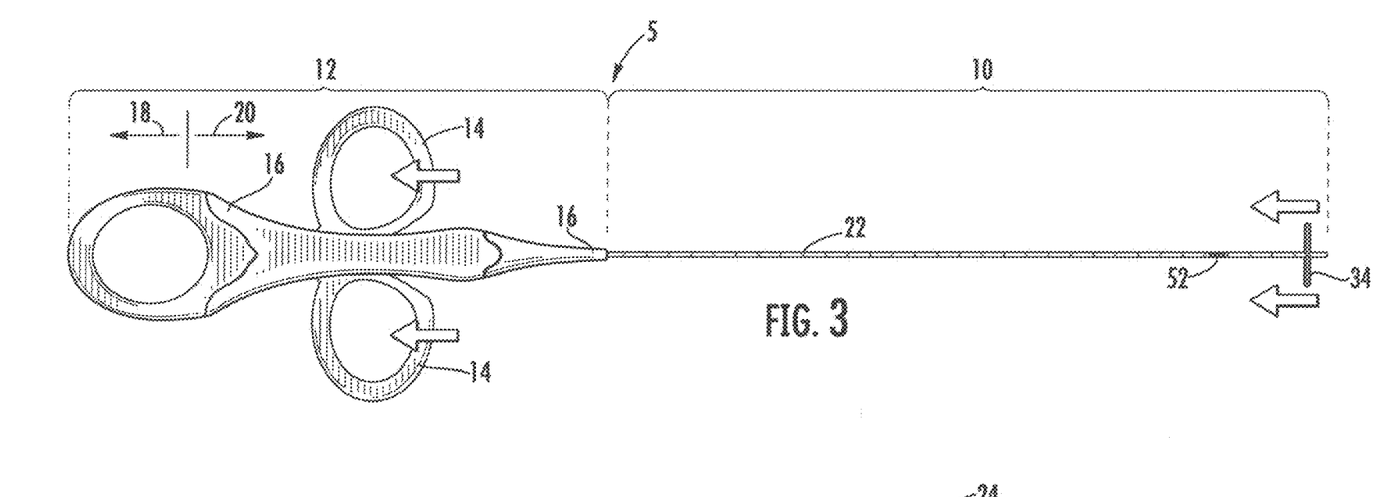
FIG. 3 is plan view of the apparatus of FIG. 1, having obtained a fully open configuration for measuring the diameter of a lumen.

An apparatus 5 according to an embodiment of the invention is illustrated in several configurations in FIGS. 1-3. As shown in FIG. 1, the apparatus 5 comprises a lumen measuring device 10 for measuring at least an inside diameter of a lumen, and a proximal handle assembly 12, for conveniently actuating relative movement of certain portions of the distal assembly. The apparatus 5 is optionally a disposable apparatus for one-time use.

With particular regard to the proximal handle assembly 12 shown in FIGS. 1-3, a first handle portion 14, relative to a second handle portion 16, is movable in a proximal direction 18 and a distal direction 20. In particular, in FIG. 1, the first handle portion 14 obtains a most proximal disposition relative to the second handle portion 16, whereas, in FIG. 3, the first handle portion 14 obtains a most distal disposition relative to the second handle portion 16. In FIG. 2, a relatively medial disposition is obtained by the first handle portion. The first handle portion 14 is constructed to receive and be grasped by two fingers of a hand, and the second handle portion 16 is constructed to receive the thumb of the hand. When the digits of the hand are so received, and the fingers and thumb are drawn together in a closing movement of the hand, the first handle portion 14 is moved in the proximal direction 18 relative to the second handle portion 16.

The handle assembly 12 may be designed to maximize grip and hand control in a surgical environment where a healthcare practitioner likely wears gloves. For example the handle assembly may comprise elastomeric portions co-molded with rigid portions. The handle assembly may be dimensioned to accommodate tenth percentile female to ninetieth percentile male hand sizes. The handle assembly may be free of sharp edges and pinch points that might otherwise snag or damage gloves and tissues. The handle assembly is preferably an ambidextrous device constructed for single-handed use in either hand (left or right). The handle assembly 12 may comprises a lock for arresting relative movement between the first handle portion 14 and second handle portion 16 and for arresting the configuration of the lumen measuring device 10. The handle assembly further optionally comprises graphical or alphanumeric markings for providing instructions for its use, information regarding its configuration, and information regarding the configuration of the lumen measuring device 10.

In the embodiment of the invention illustrated in FIGS. 1-3, the second handle portion 16 is attached to an elongate outer member 22 of the lumen measuring device 10, and the first handle portion 14 is attached to an elongate central member 24 of the lumen measuring device 10. A portion of the central member 24 generally is disposed within, is surrounded by, and is movable relative to, a portion of the outer member 22. Movement of the first handle portion 14 in the proximal direction 18 relative to the second handle portion 16 causes movement of the central member 24 in the proximal direction 18 relative to at least a portion of the outer member 22. For example, in obtaining the disposition of FIG. 3 from the disposition of FIG. 1, at least a portion of the central member 24 is retracted, in the proximal direction 18, from at least a portion of the outer member 22. The handle assembly 12 provides convenient manual control of the relative dispositions of the outer member 22 and central member 24. The disposition of the central member 24 relative to at least portions of the outer member 22 is adjustable by movement of the first handle portion 14 relative to the second handle portion 16.

The handle assembly 12 is optional, according to some embodiments of the invention, in that at least a portion of the outer member 22 of the lumen measuring device 10 is movable relative to the central member 24 without regard to whether a handle assembly is provided. Furthermore, other handle assemblies and actuating assemblies for facilitating or motivating relative movement between portions of the outer member 22 and the central member 24 are within the scope of the invention. For example, other handle assemblies include, but are not limited to: pincer assemblies; scissor-like assemblies; assemblies having gears, wheels, spools, or threaded parts for converting rotational motion into translational motion; and bolt-and-cylinder assemblies. Exemplary actuating assemblies include both manually motivated and motorized actuating parts.

Figure 5:
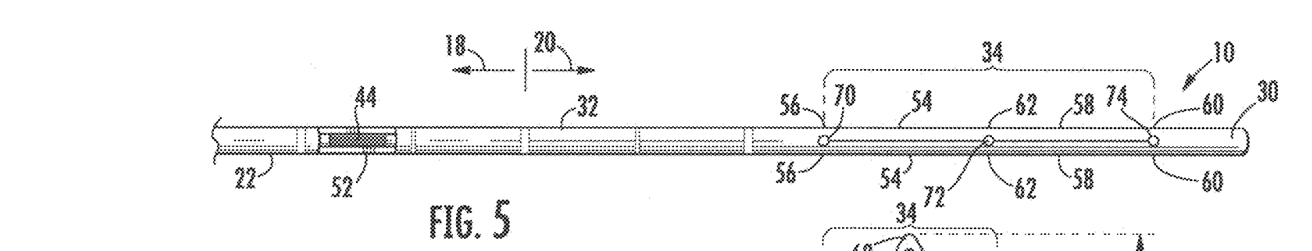
FIG. 5 is an enlarged, partial plan view of an embodiment of a lumen measuring device, having obtained a closed configuration for passage through a working channel of an endoscope and/or bronchoscope and disposition into a lumen.
Figure 6:
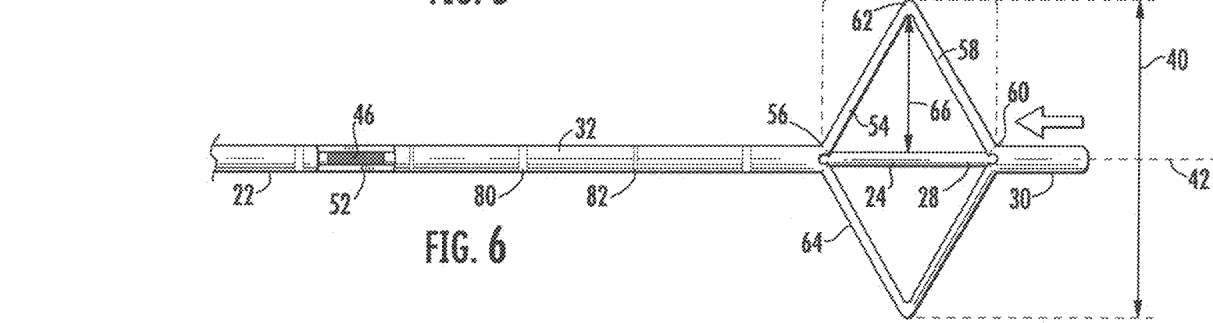
FIG. 6 is an enlarged, partial plan view of the lumen measuring device of FIG. 5, having obtained a medially open configuration for measuring the diameter of a lumen by contacting hinged linear segments of the device with the lumen.
Figure 7:
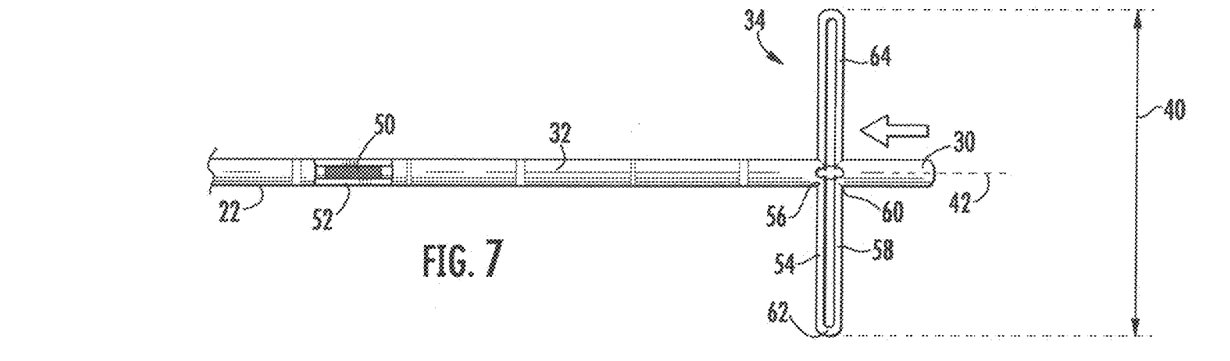
FIG. 7 is an enlarged, partial plan view of the lumen measuring device of FIG. 5, having obtained a fully open configuration for measuring the diameter of a lumen.

The lumen measuring device 10 for measuring at least an inside diameter of a lumen, according to a first embodiment of the invention, as shown in FIGS. 5-7, comprises the elongate central member 24 (FIG. 6) having a distal end 28. The central member 24 is dimensioned to extend at the distal end 28 into a lumen for measurement thereof. The device 10 further comprises the elongate outer member 22 (FIG. 5) having a fixed portion 30 (FIG. 6) fixed to the distal end 28 of the central member 24, a movable portion 32 movably extending around the central member 24, and a flexible region 34 disposed between and connecting the fixed portion 30 and movable portion 32. The flexible region 34 is configured to flex outward from the central member 24 in response to retraction of the central member relative to the movable portion 32, wherein retraction generally relates to movement of the central member 24 in the proximal direction 18 relative to the movable portion 32.

In particular, in FIG. 5, the device 10 obtains a closed configuration according to minimal retraction or no retraction of the central member relative to the movable portion 32 such that the flexible region 34 closes about the central member. In FIG. 6, the device 10 obtains a medially open configuration according to medial retraction of the central member 24 relative to the movable portion 32 such that the flexible region 34 flexes outward from the central member. In FIG. 7, the device 10 obtains a fully open configuration according to maximal retraction of the central member relative to the movable portion 32 and maximum flexing of the flexible region 34. The configuration of the device 10 is adjustable from the closed configuration of FIG. 5 to the respectively increasingly opened configurations of FIG. 6 and FIG. 7 by movement of the central member 24 in the proximal direction 18 relative to the movable portion 32 of the outer member 22.

The lumen measuring device 10 is optionally attached to the handle assembly 12 such that FIGS. 5-7 correspond respectively to FIGS. 1-3. More particularly, when the outer member 22 of the lumen measuring device 10 is attached to the second handle portion 16 and the central member 24 is attached to the first handle portion 14, the configuration of the device 10 is adjustable by movement of the first handle portion 14 relative to the second handle portion 16.

Returning to FIGS. 5-7 without regard to whether the optional handle assembly 12 of FIGS. 1-3 is attached to the lumen measuring device 10, a diameter 40 of the flexible region 34 is defined orthogonally relative the longitudinal axis 42 along which the central member is disposed. For example, in FIG. 6 the flexible region 34 comprises a pair of opposing portions and the diameter 40 is defined as the distance between outermost margins of the opposing portions.

The diameter 40 can be increased by movement of the central member 24 in the proximal direction 18 relative to the movable portion 32 of the outer member 22 until a maximum diameter 40 is obtained as shown in FIG. 7.

Figure 10:
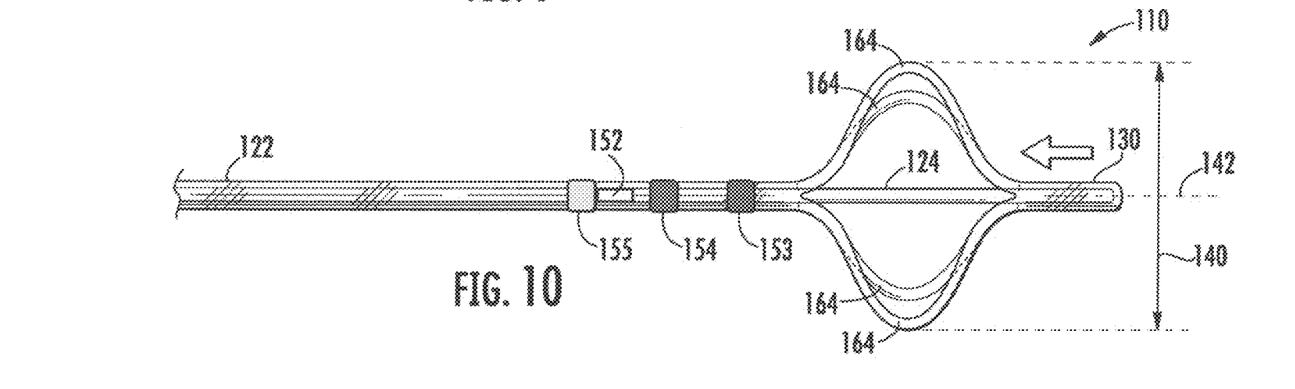
FIG. 10 is an enlarged, partial plan view of the lumen measuring device of FIG. 8, having obtained a second open configuration for measuring the diameter of a lumen.

The diameter 40 generally relates to the disposition of the central member 24 relative to the outer member 22 in a one-to-one correspondence. That is, for any particular relative disposition obtained by the central member 24, a particular configuration of the flexible region 34 is obtained having a particular diameter 40. The internal dimensions of a lumen may therefore be accomplished by increasing the diameter 40 to contact the walls of the lumen and determining the disposition of the central member. The diameter 40 is related to the disposition of the central member in a predictable way or in a way that can be empirically determined. In the embodiment illustrated in FIG. 6, the diameter 40 is related to the disposition of the central member in a way that is predictable. In FIG. 10, a diameter of a lumen measuring device is related to the disposition of a central member in a way that can be empirically determined.

According to the embodiment of the invention illustrated in FIG. 6, the diameter is predictably adjusted by movement of the central member 24 relative to the movable portion 32 of the outer member 22. In particular, a right triangle is defined in FIG. 6 having a height 66 defined as the distance between the central member and medial hinge 62, a base defined as the half distance between the hinges 56 and 60, and a hypotenuse defined by the length of the linear portion 58 of the flexible region. Movement of the central member 24 in the proximal direction 18 by any particular distance, which reduces the base of the right triangle by half that distance, results in a predictable increase in the height 66 of the triangle according to the Pythagorean theorem. As the height 66 is approximately equal to half of the diameter 40, adjustments of the diameter according to movements of the central member are therefore predictable.

The diameter 40 is therefore generally determined by determination of the disposition of the central member relative to the outer member. In order that the disposition of the central member may be determined, in the embodiment of the lumen measuring device 10 illustrated in FIGS. 5-7, the central member 24 generally defines at least one potentially viewable indicator 46. An aperture 52 is defined by the outer member such that the indicator 46 can be disposed for viewing through the aperture. When the central member 24 obtains a disposition relative to the outer member 22 such that the indicator 46 is viewable through the aperture 52 as shown in FIG. 6, the diameter 40 obtains a particular measure that may be predicted, as previously described, or may be empirically determined as described in the following with regard to FIG. 10.

The accompanying drawings are not necessarily drawn to any particular scale. The embodiments shown in the figures generally relate to lumen measuring devices for measuring various types of lumens. However, in the interest of setting forth at least one mode of carrying out at least one embodiment, the lumen measuring device 10 of at least FIGS. 5-7 is described herein in relation to measuring esophageal and bronchial lumens. With regard to length along the longitudinal axis 42, the lumen measuring device 10 therefore may be approximately ninety centimeters long for passage into oral-esophageal and oral-tracheal pathways for disposing the flexible region 34 within such lumens. The lumen measuring device 10 is preferably dimensioned for passage along the working channel, for example a two millimeter channel, of a flexible endoscope through which contact of the flexible region 34 with a host lumen may be visually confirmed.

Furthermore, one or more indicators, such as indicator 46 (FIGS. 4, 6), may be viewed through an endoscope for determination of the disposition of the central member 24 relative to the outer member 22 and for determination of the diameter 40 prescribed by the determined disposition.

Figure 4:
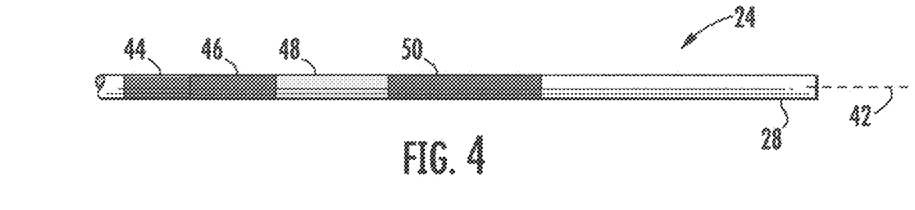
FIG. 4 is an enlarged, partial plan view of an embodiment of the central member of the lumen measuring device of FIG. 5.

With further regard toward indicators by which the disposition of the central member 24 relative to the outer member 22, and by which the diameter 40, may be determined, the exemplary embodiment of a central member, namely central member 24 of FIGS. 4-7 defines a set of graduated markings comprising the indicators 44, 46, 48, 50 sequentially defined along the central member 24 as represented without regard to any particular scale in FIG. 4. In the illustrated embodiment, each indicator 44-50 is defined by a respective colorized band portion of the central member 24. In FIG. 5, the most proximal indicator 44 is viewable through the aperture 52 defined by the outer member 22 indicating closure of the flexible region 34 and the minimum obtainable diameter thereof. In FIGS. 6 and 7, the indicators 46 and 50 are viewable indicating respective values for the diameter 40.

Various embodiments of lumen measuring devices provide various ranges of measurement according to various graduated markings on the respective central members of the embodiments. For example in FIG. 6, the indicator 46 preferably indicates a diameter 40 of approximately sixteen millimeters, whereas in FIG. 7, the indicator 50 preferably indicates a diameter 40 of approximately twenty millimeters. The indicator 48, in this example, would, if viewable through the aperture 52, indicate a diameter of approximately eighteen millimeters. The fixed portion 30 is preferably less than one centimeter in length as measured along the longitudinal axis 42.

The indicators 44, 46, 48, 50 illustrated in FIG. 4 are shown as having varying lengths along the longitudinal axis 42 because any relationship between incremental movements of the central member 24 and the correlated incremental adjustments in the prescribed diameter 40 (FIGS. 6-7) may vary according to the immediate disposition of the central member and according to the particular geometry of the flexible region 34. Indicators non-uniformly spaced or sized along of the central member 24 may correspond to regular increments in the diameter 40, for example regular two millimeter increments. Alternatively, indicators uniformly disposed or sized along the central member may correspond to irregular increments in the diameter 40.

In FIGS. 5-7, in the particular geometry illustrated, the flexible region 34 comprises an opposing pair of hinging members 64. Each hinging member comprises an elongate proximal first portion 54 hingedly attached to the movable portion 32 by a proximal hinge 56, and an elongate distal second portion 58 hingedly attached to the fixed portion 30 by a distal hinge 60. Each second portion 58 is hingedly attached to a respective first portion 54 by a respective medial hinge 62. The first portions 54 and second portions 58 each define a respective generally linear segment of the outer member such that movement of the central member 24 in the proximal direction 18 relative to the outer member 22 causes each linear segment to hinge outwardly from the central member.

In measuring the inner diameter of a host lumen, the central member 24 is generally retracted proximally relative to the movable portion 32 until the medial hinges 62 contact the lumen, as may be confirmed visually by an endoscope, such that the distance between the opposing medial hinges 62 defines the diameter 40 and corresponds to the inner diameter of the lumen at the region of contact. The inner diameter may be determined by viewing an indicator (for example indicator 46 as shown in FIG. 6) through the aperture 52 defined by the outer member by way of the endoscope.

The handle assembly 12 (FIGS. 1-3) optionally comprises a lock operatively coupled to the lumen measuring device 10 for arresting the configuration of the device 10 with regard at least to the disposition of the central member 24 relative to the outer member 22. Arresting the configuration of the lumen measuring device may be useful during placement of the device into a host lumen, during removal of the device from a host lumen, when determining contact of the flexible region with a host lumen by endoscopic viewing, and when endoscopically viewing an indicator defined by the device with regard to determining the diameter of the lumen.

The indicators 44, 46, 48, 50 are preferably defined by brightly colorized bands portions of the central member 24 that promote ease in discerning the indicators during endoscopic viewing. For example, the indicator 44 may be defined as a red colorized band, the indicator 46 may be defined as a green colorized band, the indicator 48 may be defined as a yellow colorized band, and the indicator 50 may be defined as a blue colorized band. Though four indicators preferably defined by four colorized band portions are illustrated in FIG. 4, these descriptions relate as well to any number of indicators corresponding to respective values for the diameter 40 (FIG. 6) of the flexible portion 34. In one embodiment, each particular colorized band portion corresponds to a particular stent diameter associated with the color of the band portion. Stents may be colorized according to sizes corresponding to the colorized band portions. Stents having sizes corresponding to the colorized band portions may be made available in colorized or color-coded packaging materials or encasements that correspond to the colorized band portions.

In other embodiments, the indicators 44, 46, 48, 50 (FIG. 4) sequentially defined along the central member 24 are defined by coded markings. For example, the indicators may be defined by numerical values directly representing corresponding respective values for the diameter 40 (FIG. 6). In this example, the indicator 46 may comprise numerals indicating a diameter 40 of approximately sixteen millimeters.

The outer member preferably comprises an exterior that promotes ease in discerning the indicators during endoscopic viewing. For example, the outer member 22 may comprise a colored exterior that minimizes the reflection of light from the outer member 22 and contrasts with the above-described bright colors. In particular, the exterior of the outer member 22 preferably comprises a black, grey, or muted and dull color. Additionally, the outer member 22 may comprise an exterior surface that further minimizes the reflection of light from the outer member 22. In particular, the outer member may advantageously comprise a matte exterior surface or other non-glossy exterior surface.

Whereas some lumen measuring instruments, such as that described in the U.S. Pat. No. 5,010,892, rely on elements such as a wire having a memory for an outwardly curved shape when extended from a sleeve, the lumen measuring device 10 of FIGS. 5-7 relies on generally linear segments, and hinges therebetween, that define one or more polygonal structures when the central member is retracted relative to the movable portion 32 of the outer member 22. For example, as shown in FIG. 6, the first portion 54, the second portion 58, and the central member 24 define a polygon and the height of the polygon as measured from the central member corresponds to at least a partial measure of a host lumen when the flexible region 34 contacts the lumen. In particular, the first portion 54 and second portion 58 define the sides of a triangle, that portion of the central member 24 that is disposed between the proximal hinge 56 and distal hinge 60 defines the base of the triangle, and the distance between the central member 24 and the medial hinge 62 defines the height 66 of the triangle. The height 66 of the triangle corresponds to a partial measure of a host lumen when the medial hinge 62 contacts the lumen. Insofar as the flexible region 34 defines a pair of opposing similar triangles as shown in FIG. 6, the height 66 corresponds approximately to the radius of the host lumen when the medial hinges 62 contact the lumen. The height 66 defines a dimension of a polygonal structure, namely a triangular structure in the illustrated example of FIG. 6, that is controllably adjusted by movement of the central member 24 relative to the outer member 22.

As shown in FIG. 5, the hinges 56, 62, 60 may be defined by respective small holes 70, 72, 74 uniformly spaced and formed through the flexible region 34 of the outer member 22. The hinges 56, 62, 60 are formed as discrete thinned portions of the flexible region 34 wherein flexing of the region generally obtains hinging of the thinned portions while the first and second portions 54, 58 are generally maintained as linear segments.

The lumen measuring device 10, as shown in FIG. 2, comprises depth indicators, for example along the outer member 22. In particular, major depth indicators 80 preferably correspond to particular length increments along the outer member, for example centimeters, whereas minor depth indicators 82 preferably correspond to halves of the particular length increments, for example half centimeters. The axial indicators are potentially useful for determining the disposition of any portion of the lumen measuring device relative to an orifice, an incision, or a working channel of an endoscope, through which the device is passed. The depth indicators are furthermore potentially useful for measuring the length of a lumen stricture, and, when a diameter of a lumen is measured, for determining the location of the measurement along the length of the lumen.

The lumen measuring device 10 relates to measuring longitudinal and transverse dimensions of a lumen. The depth indicators 80, 82 (FIG. 6) relate to longitudinal dimensions such the length of a lumen and the indicators 44, 46, 48, 50 (FIG. 4) relate to transverse dimensions such as the diameter of a lumen. A particular lumen or a portion thereof may obtain a cross-sectional shape that is not precisely, or even approximately, round. The lumen measuring device may be rotated about the longitudinal axis 42 for diameter 40 measurements that vary with the rotation. The flexible region 34 may be disposed at a prescribed or determined position along the length of a lumen with attention toward the depth indicators 80, 82, which provide for measurements in a first spatial dimension. Cross-sectional dimensions of the lumen at that position may be measured with attention toward the indicators 44, 46, 48, 50, which provide for measurements in a second spatial dimension, and by way rotation of the device 10 about the longitudinal axis 42, may provide for measurements in a third spatial dimension. Thus, in the embodiment of the lumen measuring device 10 of FIGS. 4-7, measurements of the interior of a lumen, conduit, or partially enclosed space are provided in up to three dimensions by way of indicators 80, 82 and 44, 46, 48, 50 which are disposed along a single axis 42 of the device.

Figure 8:
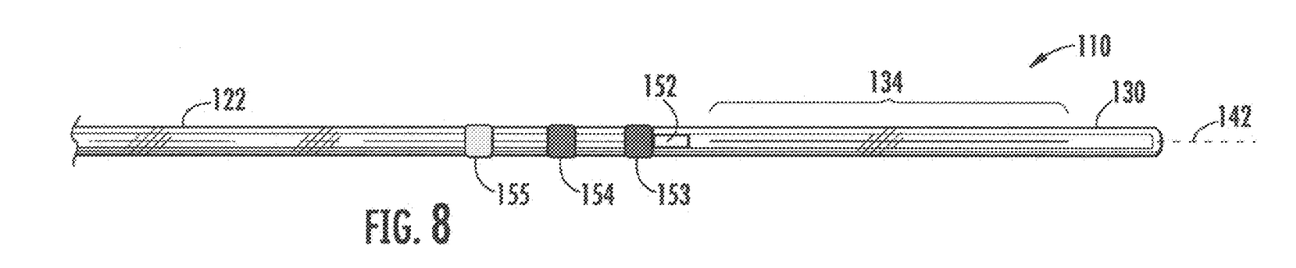
FIG. 8 is an enlarged, partial plan view of another embodiment of a lumen measuring device, having obtained a closed configuration for passage through a working channel of an endoscope and disposition into a lumen.
Figure 9:
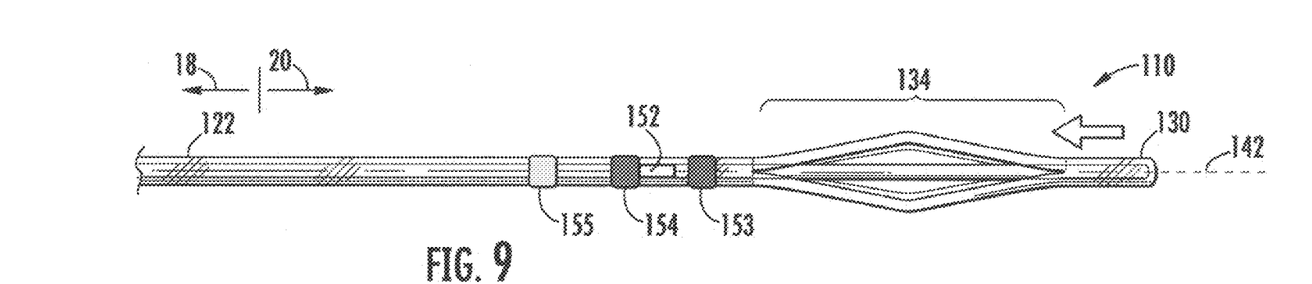
FIG. 9 is an enlarged, partial plan view of the lumen measuring device of FIG. 8, having obtained a first open configuration for measuring the diameter of a lumen by contacting arcuately bowed members of the device with the lumen.

In another embodiment, as shown in FIGS. 8-10, a lumen measuring device 110 comprises an elongate central member 124 (FIG. 10) generally disposed within an outer member 122. The outer member comprises a fixed portion 130 fixed to the distal end of the central member 124, a movable portion 132 movably extending around the central member 124, and a flexible region 134 disposed between and connecting the fixed portion 130 and movable portion 132. The flexible region 134 flexes outward from the central member 124 in response to retraction of the central member relative to the movable portion 132, wherein retraction generally relates to movement of the central member 124 in the proximal direction 18 relative to the movable portion 132 along the longitudinal axis 142.

The lumen measuring device 110 of FIGS. 8-10 possesses similarities to the lumen measuring device 10 of FIGS. 5-7. However, the lumen measuring device 110 also possesses differences relative to the lumen measuring device 10. For the sake of brevity and in order to avoid unnecessarily repetitive descriptions, the differences are preferentially described herein. For example, with regard to the device 10, linear segments of the flexible region 34 hinge away from the central member 24 about defined hinges in FIG. 6 such that flexure is concentrated at the hinges 56, 62, and 60. In difference to FIG. 6, flexing members 164 of FIG. 10 arcuately bow outwardly from the central member 124 in that flexure is generally distributed across the length of each flexing members. The flexing members 164 are disposed about the longitudinal axis 142 and arcuate outward extremes of the flexing members together define a diameter 140 of the flexible region 134. When the flexing members 164 are observed to contact a lumen, for example by way of endoscopic viewing, the diameter 140 obtains a value approximately equivalent to the inner diameter of the lumen at the region of contact. While four flexing members are shown in FIG. 10, these descriptions relate as well to any odd or even number of flexing members.

The flexing of the members 164 relates to the disposition of the central member 124 in a fashion that is repeatable according to the flexible but semi-rigid properties of the members. Thus, each possible disposition of the central member corresponds to a particular measure of the diameter 140 that may or may not be predicted but that can be at least empirically determined and can be therefore calibrated by trials. Such determination and calibration can be conducted by the manufacturer or user of the device 110. With such calibration accomplished, measuring the diameter of a lumen entails expanding the flexible region 134 such that the members contact the lumen, then determining the disposition of the central member relative to the outer member.

In order to facilitate the determination of the relative disposition of the central member, the outer member 122 is generally translucent or transparent such that an indicator 152 of the central member is generally viewable through the outer member 122. The outer member 122 comprises a number of indicators, for example indicators 153, 154, 155. The disposition of the central member 124 relative to the outer member 122 is discerned by determining the disposition of the indicator 152 relative to the indicators 153, 154, 155. In the illustrated embodiment, the indicators 153, 154, 155 are uniformly spaced along the outer member though in other embodiments non-uniformly spaced dispositions prevail. The disposition of the indicator 152 adjacent the indicator 153 in FIG. 8 corresponds to the region 134 obtaining an unflexed, closed configuration such that the region 134 closes about the central member. The disposition of the indicator 152 adjacent the indicator 155 in FIG. 10 corresponds to the flexible region 134 obtaining a flexed, open configuration and corresponds to a particular value for the diameter 140 defined by the flexing members 164. The indicators 153, 154, and 155 are optionally respectively colorized so that the disposition of the central member relative to the outer member is unambiguously discerned by viewing the indicator 152 in relation to the indicators 153, 154, and 155.

The outer members of lumen measuring devices described herein preferably comprise low friction tubular material such as smooth plastic for facilitating passage through the working channel of an endoscope and insertion into a lumen with little resistance. The distal ends of the outer members are preferably atraumatic in that they define rounded, beveled, or arcuate end portions of the lumen measuring devices to minimize risks of perforating lumens and risks of other tissue damages.

The central members described herein may comprise cylindrical metallic rods constructed of, for example, stainless steel. The central members and outer members are preferably flexible about their longitudinal axes for passage through arcuate pathways. The central members and the movable portions of the outer members are preferably inextensible and incompressible along their longitudinal axes for maintaining their longitudinal integrities providing accurate measurements.

The lumen measuring devices described herein optionally comprise radiopaque markers. Radiopaque materials generally block the transmission of X-rays and other penetrating fields and radiopaque markers therefore are generally visible in a fluoroscopic or X-ray image. For example, with regard to the lumen measuring device 10 of FIG. 6, the depth indicators 80, 82 may comprise radiopaque material and the indicators 44, 46, 48, 50 (FIG. 4) may comprise radiopaque material. For further example, with regard to the lumen measuring device 110 of FIGS. 8-10, the indicators 152, 153, 154, 155 may comprise radiopaque material.

The embodiments of the present invention that are detailed in the preceding descriptions provide many advantages. For example, the lumen measuring device 10 (FIGS. 5-7), and the lumen measuring device 110 (FIGS. 8-10), each comprise flexing members that are attached at their proximal and distal ends to the device such that medial portions of the flexing members flex outwardly for contacting and measuring a lumen. This is advantageous over lumen measuring devices that have free-ended measuring members constructed of shape-memory materials in that the flexing members of the invention define stable repeatable structures that are predictably or empirically calibrated with regard to measuring the diameter of a lumen. Polygonal structures, such as the triangles defined by the flexible region 34 of the device 10 of FIGS. 5-7, may be particularly advantageous with regard to predictable calibrations, repeatable performances, and accurate measurements of lumen dimensions. For another example of an advantage provided by the invention, indicators 44, 46, 48, 50 appearing on the central member 24 in FIG. 4 are preferably brightly colorized bands for unambiguous identification of a stent size for the measured lumen.

Each of co-pending U.S. non-provisional patent application Ser. No. 10/618,223 of Mangiardi et al., filed Jul. 11, 2003, the publication thereof, namely United States patent application publication number US2005/0010138A1, published Jan. 13, 2005, and co-pending U.S. non-provisional patent application Ser. No. 10/404,197 of Mangiardi et al., filed Mar. 31, 2003, and the publication thereof, namely United States patent application publication number US2004/0193243A1, are incorporated herein by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A lumen measuring device for measuring at least an inside diameter of a lumen by extending the device into the lumen, said lumen measuring device comprising:
   a) an elongate central member having a proximal end and a distal end; and
   b) an elongate outer member having a proximal end and a distal end and being integrally formed from a single piece of tubular material, the outer member including,
      (i) a fixed portion at the distal end fixed to the distal end of the central member,
      (ii) a movable portion movably extending around the central member, and
      (iii) a flexible region disposed between and connecting said fixed portion and said movable portion, the flexible region configured to flex outward from the central member in response to retraction of the central member relative to the movable portion of the elongate outer member,
      (iv) wherein the elongate outer member comprises an outer diameter, and wherein the outer diameter of the outer member is the same between its proximal and distal ends before the flexible region is flexed;
   c) wherein flexing of said flexible region causes it to contact the lumen and indicate the inside diameter of the lumen, and
   d) a first handle portion coupled to the central member and a second handle portion coupled to the outer member, wherein the first and second handle portions are displaceable with respect to one another, and
   e) a first part of the first handle portion being disposed within the second handle portion, the first part of the first handle portion having proximal and distal ends,
   f) wherein displacement of the first handle portion in the proximal direction relative to the second handle portion is limited by contacting the proximal end of the first part of the first handle portion with a first part of the second handle portion disposed proximal to the first part of the first handle portion, and
   g) wherein displacement of the first handle portion in the distal direction relative to the second handle portion is limited by contacting the distal end of the first part of the first handle portion with a second part of the second handle portion disposed distal to the first part of the first handle portion, and
   h) a second part of the first handle portion extending out of the second handle portion and comprising a first loop configured to receive a first user's finger, and
   i) a third part of the first handle portion extending out of the second handle portion opposite the second part of the first handle portion, the third part of the first handle portion comprising a second loop configured to receive a second user's finger,
   j) wherein the second handle portion comprises a third loop configured to receive a user's thumb, the third loop being disposed proximal to the first part of the second handle portion.

2. The lumen measuring device of claim 1, wherein the flexible region of the outer member comprises at least two hinging members connected to the fixed portion of the outer member, wherein hinging of said hinging members causes contact thereof with the lumen in response to retraction of the central member relative to the movable portion of the elongate outer member.

3. The lumen measuring device of claim 1, wherein the flexible region of the outer member comprises a plurality of flexing members, wherein retraction of the central member relative to the movable portion causes said flexing members to contact the lumen.

4. The lumen measuring device of claim 1, wherein the flexible region of the outer member comprises a plurality of flexing members each having a proximal end attached to the movable portion and a distal end attached to the fixed portion.

5. The lumen measuring device of claim 4, wherein retraction of the central member relative to the movable portion causes each said flexing member to arcuately bow outwardly from the central member.

6. The lumen measuring device of claim 4, wherein each said flexing member has at least a generally linear segment, and wherein retraction of the central member relative to the movable portion causes a linear segment of each flexing member to hinge outwardly from the central member.

7. The lumen measuring device of claim 1, wherein the flexible region of the outer member comprises a plurality of hinging members, each said hinging member comprising:
   an elongate first portion hingedly attached to said movable portion by a proximal hinge defined between the first portion and movable portion; and
   an elongate second portion hingedly attached to said fixed portion by a distal hinge defined between the second portion and fixed portion;
   wherein said second portion is hingedly attached to said first portion by a medial hinge defined between the second portion and first portion.

8. The lumen measuring device of claim 7, wherein retraction of said central member relative to said movable portion causes said medial hinge to contact the lumen.

9. The lumen measuring device of claim 7, wherein a first said hinging member opposes a second said hinging member, wherein retraction of said central member relative to said movable portion causes the medial hinge of the first hinging member to contact the lumen and causes the medial hinge of the second hinging member to contact the lumen such that the distance between the two medial hinges provides a measure of the inside diameter of the lumen.

10. The lumen measuring device of claim 7, wherein the first portion and second portion define the sides of a triangle, wherein the central member defines the base of the triangle, wherein the distance of the medial hinge from the central member defines the height of the triangle corresponding to at least a partial measure of the inside diameter of the lumen.

11. The lumen measuring device of claim 1, wherein the flexible region defines a polygon at least two sides of which hinge away from the central member in response to retraction of the central member relative to the movable portion of the elongate outer member, wherein the height of the polygon measured from the central member corresponds to at least a partial measure of the inside diameter of the lumen.

12. The lumen measuring device of claim 1, wherein generally linear segments of the flexible region define the sides of a polygonal structure, wherein the linear segments hinge away from central member and contact the lumen in response to retraction of the central member relative to the movable portion of the outer member.

13. The lumen measuring device of claim 1, wherein at least one dimension of a polygonal structure defined by linear segments of the flexible region is controllably adjusted by movement of the central member relative to the outer member.

14. The lumen measuring device of claim 13, wherein one or more indicators defined by the central member are viewable for indicating at least one dimension of the polygonal structure and for indicating the inside diameter of the lumen when the flexible region contacts the lumen.

15. The lumen measuring device of claim 14, wherein said one or more indicators are defined by one of more colored regions of the central member.

16. The lumen measuring device of claim 1, wherein the central member has colored regions which are viewable for indicating the disposition of the central member relative to the outer member.

17. The lumen measuring device of claim 1, wherein the central member has colored regions that are controllably viewable according to the disposition of the central member relative to the outer member.

18. The lumen measuring device of claim 1, wherein one or more colored regions of the central member are viewable through an aperture defined by said movable portion.

19. The lumen measuring device of claim 1, wherein at least one indicator defined by the central member is viewable through an aperture defined in the outer member.

20. The lumen measuring device of claim 1, wherein at least one indicator is defined by the central member, and wherein multiple indicators are defined by the outer member.

21. The lumen measuring device of claim 20, wherein colored regions of the outer member define said multiple indicators.

22. The lumen measuring device of claim 1, wherein depth indicators are viewable along said outer member.

23. The lumen measuring device of claim 1, wherein the first handle portion is attached to the proximal end of the central member and the second handle portion is attached to the proximal end of the outer member, wherein the disposition of the central member relative to the outer member is adjustable by movement of the first handle portion relative to the second handle portion.

24. The lumen measuring device of claim 23, wherein engagement between the first handle portion relative to the second handle portion at a proximal most disposition of the central member relative to the outer member corresponds to a position wherein the flexible region is not flexed outwardly, and wherein an engagement between the first handle portion relative to the second handle portion at a distal most disposition of the central member relative to the outer member corresponds to a distal most position wherein the flexible region is flexed outwardly to its maximum diameter.

25. The lumen measuring device of claim 1, wherein the elongate outer member comprises an outer diameter, and wherein the outer diameter of the outer member is substantially the same between its proximal and distal ends.

26. The lumen measuring device of claim 1, wherein the first handle portion and the second handle portion each comprises at least one hole for receiving a user's digit and facilitating the displacement of the first and second handle portions with respect to one another.

27. The lumen measuring device of claim 26, wherein the first handle portion comprises a pair of holes and the second handle portion comprises a single hole such that a user is capable of displacing the first and second handle portions with one hand.

28. A method of measuring an interior dimension of a lumen, the method comprising:
   a) providing a device comprising an elongate assembly and a handle, the elongate assembly comprising an elongate central member having a proximal and a distal end and an elongate outer member having a proximal and a distal end, the elongate outer member integrally formed from a single piece of tubular material, the outer member including, (i) a fixed portion at the distal end fixed to the distal end of the central member,
(ii) a movable portion movably extending around the central member, and
(iii) a flexible region disposed between and connecting said fixed portion and said movable portion, the flexible region configured to flex outward from the central member in response to retraction of the central member relative to the movable portion of the elongate outer member;

wherein the elongate outer member comprises an outer diameter, and wherein the outer diameter of the outer member is the same between its proximal and distal ends before the flexible region is flexed, the handle comprising a first handle portion coupled to the proximal end of the central member and a second handle portion coupled to the proximal end of the outer member wherein the first and second handle portions are displaceable with respect to one another, and wherein:

i) a first part of the first handle portion is disposed within the second handle portion, the first part of the first handle portion having proximal and distal ends, wherein displacement of the first handle portion in the proximal direction relative to the second handle portion is limited by contacting the proximal end of the first part of the first handle portion with a first part of the second handle portion disposed proximal to the first part of the first handle portion, and wherein displacement of the first handle portion in the distal direction relative to the second handle portion is limited by contacting the distal end of the first part of the first handle portion with a second part of the second handle portion disposed distal to the first part of the first handle portion, and ii) a second part of the first handle portion extends out of the second handle portion, the second part of the first handle portion comprising a first loop configured to receive a first user's finger, and iii) a third part of the first handle portion extends out of the second handle portion opposite the second part of the first handle portion, the third part of the first handle portion comprising a second loop configured to receive a second user's finger, wherein the second handle portion comprises a third loop configured to receive a user's thumb, the third loop being disposed proximal to the first part of the second handle portion;

b) disposing a distal portion of the elongate assembly into a lumen;

c) retracting a portion of the elongate central member of the assembly within a portion of the elongate outer member of the assembly causing the flexible region of the outer member to flex outwardly from the central member such that portions of the flexible region contact the lumen;

d) measuring an interior dimension of the lumen by determining the disposition of the central member relative to the outer member, wherein said step of retracting a portion of the central member comprises retracting the first handle portion relative to the second handle portion.

29. The method of claim 28, wherein said step of retracting a portion of the central member comprises retracting a proximal portion of the central member along the longitudinal axis of a proximal portion of the outer member while a distal portion of the central member remains fixed relative to a distal portion of the outer member, and wherein said step of retracting a portion of the central member causes the distal portion of the outer member to move relative to the proximal portion of the outer member.

30. The method of claim 28, wherein said step of retracting a portion of the central member causes linear segments of the flexible region to hinge outwardly from the central member.

31. The method of claim 28, wherein said step of retracting a portion of the central member causes linear segments of the flexible region to hinge outwardly from the central member such that a polygon is defined at least in part by the linear segments.

32. The method of claim 28, wherein the step of determining the disposition of the central member relative to the outer member comprises viewing colored portions of the central member.

33. The method of claim 28, wherein said step of retracting a portion of the central member comprises positioning a user's digit within at least one hole defined in each of the first and second handle portions and displacing the first and second handle portions with respect to one another.

34. A lumen measuring device for measuring at least an inside diameter of a lumen by extending the device into the lumen, said lumen measuring device comprising:

a) an elongate central member having a proximal end and a distal end; and b) an elongate outer member having a proximal end and a distal end and being integrally formed from a single piece of tubular material, the outer member including,
(i) a fixed portion at the distal end fixed to the distal end of the central member,
(ii) a movable portion movably extending around the central member, and
(iii) a flexible region disposed between and connecting said fixed portion and said movable portion, the flexible region consisting of a pair of diametrically opposed hinging members defined by a pair of parallel slots extending between the fixed portion and the movable portion, the pair of hinging members configured to flex outward from the central member in response to retraction of the central member relative to the movable portion of the elongate outer member
(iv) wherein the elongate outer member comprises an outer diameter, and wherein the outer diameter of the outer member is the same between its proximal and distal ends before the flexible region is flexed;

c) wherein flexing of said flexible region causes the pair of hinging members to contact the lumen and indicate the inside diameter of the lumen, and d) a first handle portion coupled to the central member and a second handle portion coupled to the outer member, wherein the first and second handle portions are displaceable with respect to one another, and e) a first part of the first handle portion being disposed within the second handle portion, the first part of the first handle portion having proximal and distal ends, f) wherein displacement of the first handle portion in the proximal direction relative to the second handle portion is limited by contacting the proximal end of the first part of the first handle portion with a first part of the second handle portion disposed proximal to the first part of the first handle portion, and g) wherein displacement of the first handle portion in the distal direction relative to the second handle portion is limited by contacting the distal end of the first part of the first handle portion with a second part of the second handle portion disposed distal to the first part of the first handle portion, and h) a second part of the first handle portion extending out of the second handle portion and comprising a first loop configured to receive a first user's finger, and i) a third part of the first handle portion extending out of the second handle portion opposite the second part of the first handle portion, the third part of the first handle portion comprising a second loop configured to receive a second user's finger, j) wherein the second handle portion comprises a third loop configured to receive a user's thumb, the third loop being disposed proximal to the first part of the second handle portion.

35. A lumen measuring device for measuring at least an inside diameter of a lumen by extending the device into the lumen, said lumen measuring device comprising:

a) an elongate central member having a proximal end and a distal end, the central member comprising a plurality of viewable indicators; and b) an elongate outer member having a proximal end and a distal end and being integrally formed from a single piece of tubular material, the outer member including,
   (i) an aperture formed such that a viewable indicator can be disposed for viewing through the aperture,
   (ii) a fixed portion at the distal end fixed to the distal end of the central member,
   (iii) a movable portion movably extending around the central member, and
   (iv) a flexible region disposed between and connecting said fixed portion and said movable portion, the flexible region configured to flex outward from the central member in response to retraction of the central member relative to the movable portion of the elongate outer member, c) wherein flexing of said flexible region causes it to contact the lumen and indicate the inside diameter of the lumen, and d) a first handle portion coupled to the central member and a second handle portion coupled to the outer member, wherein the first and second handle portions are displaceable with respect to one another, wherein the first handle portion is constructed to receive a first digit of a user's hand and the second handle portion is constructed to receive a second digit of the hand, and wherein said first handle portion and said second handle portion are configured to be displaced with one hand, wherein a first part of the first handle portion is disposed within the second handle portion, the first part of the first handle portion having proximal and distal ends, wherein displacement of the first handle portion in the proximal direction relative to the second handle portion is limited by contacting the proximal end of the first part of the first handle portion with a first part of the second handle portion disposed proximal to the first part of the first handle portion, and wherein displacement of the first handle portion in the distal direction relative to the second handle portion is limited by contacting the distal end of the first part of the first handle portion with a second part of the second handle portion disposed distal to the first part of the first handle portion.

36. The lumen measuring device of claim 35 wherein the elongate outer member comprises an outer diameter, and wherein the outer diameter of the outer member is the same between its proximal and distal ends before the flexible region is flexed.

37. The lumen measuring device of claim 35, wherein a second part of the first handle portion extends out of the second handle portion and comprises a first loop configured to receive a first user's finger, and a third part of the first handle portion extends out of the second handle portion opposite the second part of the first handle portion, the third part of the first handle portion comprising a second loop configured to receive a second user's finger, and wherein the second handle portion comprises a third loop configured to receive a user's thumb, the third loop being disposed proximal to the first part of the second handle portion.

* * * * *